United States Patent
Thibodeau et al.

(10) Patent No.: US 7,063,849 B1
(45) Date of Patent: Jun. 20, 2006

(54) USE OF HIV-1 GP120 AND GP160 PROTEINS MODIFIED IN THE V3 LOOP FOR THE PREPARATION OF VACCINE COMPOSITIONS AND FORMULATIONS CONTAINING THE SAME

(75) Inventors: Lise Thibodeau, Montreal (CA); Claude Lavallee, Springfield, NJ (US)

(73) Assignee: Fondation Mondiale Recherche et Prevention Sida, Paris (FR)

( * ) Notice: Subject to any disclaimer, the term of this patent is extended or adjusted under 35 U.S.C. 154(b) by 699 days.

(21) Appl. No.: 09/632,806

(22) Filed: Aug. 4, 2000

(30) Foreign Application Priority Data

Apr. 4, 2000 (FR) .................................. 00 04310

(51) Int. Cl.
*A61K 39/21* (2006.01)

(52) U.S. Cl. ................................ 424/188.1; 424/208.1
(58) Field of Classification Search ............. 424/188.1, 424/208.1
See application file for complete search history.

(56) References Cited

U.S. PATENT DOCUMENTS 5,910,306 A * 6/1999 Alving et al. ............ 424/184.1
6,048,531 A * 4/2000 Mannino et al. ......... 424/194.1

OTHER PUBLICATIONS

Hoth, D. F., et al., 1994, "HIV vaccine development: a progress report", Ann. Int . Med. 8(7):603-611.*
Stott, J., and N. Almond, 1995, "Assessing animal models of AIDS", Nat. Med. 1(4):295-297.*
Graham, B. S., and P. F. Wright, 1995, "Candidate AIDS vaccines", New Engl. J. Med. 333(20):1331-1339.*
Haynes, B. F., et al., 1996, "Update on the issues of HIV vaccine development", Ann. Med. 28:39-41.*
Haynes, B. F., 1996, "HIV vaccines: where we are and where we are going", Lancet 348:933-937.*
Kent, S. J., et al., 1997, "Antagonism of vaccine-induced HIV-1-specific CD4+ T cells by primary HIV-1 infection", J. Immunol. 158:807-815.*
Lee, T.-H., 1997, "Acquired immunodeficiency disease vaccines: design and development", in *AIDS: Biology, Diagnosis, Treatment and Prevention, fourth edition*, DeVita, Jr., V. T., et al., eds., Lippincott-Raven Publishers, Philadelphia, PA, pp. 605-616.*

Letvin, N. L., 1998, "Progress in the development of an HIV-1 vaccine", Science 280:1875-1880.*
Burton, D. R., and J. P. Moore, 1998, "Why do we not have an HIV vaccine and how we can we make one?", Nat. Med. 4(5):495-498.*
Moore, J. P., and D. R. Burton, 1999, "HIV-1 neutralizing antibodies: how full is the bottle?", Nat. Med. 5(2):142-144.*
Nathanson, N., and B. J. Mathieson, 2000, "Biological considerations in the development of a human immunodeficiency virus vaccine", J. Infect. Dis. 182:579-589.*
Johnston, M. I., 2000, "The role of nonhuman primate models in AIDS vaccine development", Mol. Med. 6:267-270.*
Bende, S., and M. I. Johnston, 2000, "Update: search for an AIDS vaccine", AIDS Reader, Sep., 526-538.*
Feinberg, M. B., and J. P. Moore, 2002, "AIDS vaccine models: challenging challenge viruses", Nat. Med. 8(3):207-210.*
Lavallee, C., and L. Thibodeau, 1996, "Clonage, expression et caracterisation de gp160 du VIH-1, portant des deletions partielles ou totales dans la boucle V3", C.R. Acad. Sci. Paris, Sciences de la vie/Life sciences, 319:983-990.*

(Continued)

*Primary Examiner*—Jeffrey S. Parkin
(74) *Attorney, Agent, or Firm*—Morgan, Lewis & Bockius

(57) ABSTRACT

Use of HIV-1 gp120 and gp160 proteins which have been modified in the V3 loop for preparing vaccine compositions and formulations containing them which induce a systemic and mucosal immunity.

Use of a recombinant HIV-1 Env protein, in which the V3 loop is partially or completely deleted, for preparing a vaccine composition which is capable of inducing an immunity which is at the same time humoral, cellular and mucosal with respect to HIV-1.

The vaccine composition comprises:

a recombinant Env protein as defined above, optionally at least one compound selected from the group consisting of: (1) the vaccination adjuvants selected from the group consisting of derivatives comprising divalent or trivalent ions: aluminium hydroxide or calcium phosphate, and muramylpeptide derivatives and (2) liposomes and optionally at least one pharmaceutically acceptable vehicle.

11 Claims, No Drawings

OTHER PUBLICATIONS

Burton, D. R., et al., 1998, "Why do we not have HIV vaccine and how can we make one?", Nature Med. Vaccine Suppl. 4(5):495-498.*

Moore, J. P., et al., 1999, "HIV-1 neutralizing antibodies: how full is the bottle?", Nature Med. 5(2):142-144.*

* cited by examiner

SEQUENCE LISTING

```
<160> NUMBER OF SEQ ID NOS: 1

<210> SEQ ID NO 1
<211> LENGTH: 6
<212> TYPE: PRT
<213> ORGANISM: Human immunodeficiency virus type 1
<220> FEATURE:
<221> NAME/KEY: MISC_FEATURE
<223> OTHER INFORMATION: Hexamer sequence derived from V3 loop of
      envelope protein

<400> SEQUENCE: 1

Gly Pro Gly Arg Ala Phe
1               5
```

USE OF HIV-1 GP120 AND GP160 PROTEINS MODIFIED IN THE V3 LOOP FOR THE PREPARATION OF VACCINE COMPOSITIONS AND FORMULATIONS CONTAINING THE SAME

The present invention relates to the use of HIV-1 gp120 and gp160 proteins which have been modified in the V3 loop for preparing vaccine compositions, as well as to formulations containing them which are capable of producing a humoral, cellular and mucosal immune response.

The type-1 human immunodeficiency virus (HIV-1) is the aetiological agent of AIDS. HIV-1 induces a persistent infection in humans which leads to a severe immunodeficiency. The envelope of HIV is composed of two glycoproteins, gp120 and gp41, which are derived from a precursor, gp160, by proteolytic cleavage. Five conserved regions, C1 to C5, and five variable regions, V1 to V5, have been demonstrated in the glycoprotein of the envelope. Three functional regions play an essential role in the first steps of the infection, and have been identified: the CD4-binding site (in the C4 region), the V3 region, which is essential to infectivity, and finally a very hydrophobic region which is located at the N-terminal end of gp41, and which participates in the fusion between the membrane of the target cell and the viral envelope. The V3 loop is hypervariable, immunodominant and corresponds to the principal neutralizing-antibody-inducing determinant (PND).

It is generally accepted that neutralizing antibodies play an important role in protection against viral infection (1, 2).

However, in the case of the type 1 human immunodeficiency virus (HIV-1), the neutralizing antibodies which develop at an early stage of the infection do not prevent the progression of the disease.

Specifically, in infected individuals, the neutralizing antibodies, when they exist, exhibit a very narrow neutralization range and often do not neutralize the strain(s) which infect(s) the patient (3, 4). In the same way, the neutralizing antibodies induced by vaccination with gp160/120 in solution are generally specific for the strain used for the vaccine preparation and are directed against one or more determinants in the V3 loop of gp120 (5).

Although the V3 loop is hypervariable, a Gly-Pro-Gly-Arg (GPGR) (amino acid residues 1–4 of SEQ ID NO: 1) tetrapeptide which is located at the top of the loop, as well as two cysteines at its base, are present in almost all known isolates of HIV-1, which indicates that this sequence is essential to a vital cycle step of the virus (6).

The roles of the V3 loop (cellular tropism, infectivity, induction of restricted-range neutralizing antibodies and role in pathogenesis) have been demonstrated (6).

The inventors have modified the env gene of HIV-1 by carrying out deletions which eliminate or decrease the hypervariable epitopes of the V3 loop. The results, obtained with a partial deletion in the V3 loop of gp160 while keeping the tip of the V3 loop, i.e. the GPGRAF (SEQ ID NO: 1) sequence and the two cysteines at its base, show that the modified protein ΔV3-GPGRAF is expressed in the same way as the unmodified protein, and that it reacts with an anti-HIV human reference serum to a degree which is similar to unmodified recombinant gp160 (7).

A protein in which the V3 loop is completely deleted was also produced; it is the protein ΔV3+, which is also expressed and which has a molecular mass compatible with the deletion.

This set of elements has led the inventors to formulate the hypothesis that the V3 loop would represent a decoy for the immune system, and that the modification or elimination of this loop might induce a conformational change in the molecule, which would reveal itself by the induction of a neutralizing activity directed against other epitopes which are more conserved but which show weak immunogenicity during the natural infection or subsequent to a vaccination with the native protein.

Faced with the AIDS epidemic, the development of an anti-AIDS vaccine which is capable of halting the propagation of the disease is imperative; indeed, the World Health Organization estimates that in 2002, there could be between 50 and 75 million people in the world infected with HIV.

The inventors consequently gave themselves the goal of producing a vaccine composition which is better at meeting the requirements of the art in that it is capable of inducing a humoral, cellular and mucosal immune response which exhibits a wide-ranging neutralization due to the induction of antibodies which are capable of neutralizing various types of HIV-1 strain, and in particular both laboratory strains and clinical strains (primary isolates).

A subject of the present invention is the use of a recombinant HIV-1 Env protein, in which the V3 loop is partially or completely deleted, for preparing a vaccine composition which is capable of inducing an immunity which is at the same time humoral, cellular and mucosal with respect to divergent strains of HIV-1.

The inventors have now found, surprisingly, that the proteins in which the V3 loop is partially or completely deleted are actually capable of inducing a wide-ranging protective immunity which is at the same time humoral (neutralizing antibodies), cellular (cytotoxic T lymphocytes) and mucosal (neutralizing secretory IgA productions).

"Wide-ranging immune response or immunity" is intended to mean the set of humoral and cellular factors which protects the body against an HIV-1 infection, in accordance with the definition by J. F. Bach (Immunology Treaty, Flammarion, 1993).

In accordance with said use, said recombinant Env protein is selected from the group consisting of the Env proteins in which the V3 loop is partially deleted: ΔV3-GPGRAF recombinant gp160 and gp120 proteins, and the Env proteins in which the V3 loop is completely deleted: ΔV3+ recombinant gp160 and gp120 Env proteins.

A subject of the present invention is also a vaccine composition, characterized in that it comprises:
a recombinant Env protein as defined above,
optionally at least one compound selected from the group consisting of:
(1) the vaccination adjuvants selected from the group consisting of derivatives comprising divalent or trivalent ions: aluminium hydroxide or calcium phosphate, and muramylpeptide derivatives and
(2) liposomes and
optionally at least one pharmaceutically acceptable vehicle.

According to one advantageous embodiment of said vaccine composition, it comprises a recombinant Env protein as defined above which is anchored onto unilamellar synthetic lipid vesicles or liposomes (immunosomes) which comprise a phosphatidylcholine:cholesterol molar ratio of about 8:1, and which have a size of between 70 and 150 nm, preferably 90 nm, as described in patent EP 47480.

Such a vaccine composition can advantageously be administered either generally or systemically: orally, parenterally, or locally (via the rectal or vaginal route, for example); it is preferably administered via a route which involves a direct contact with a mucous membrane, and which thus makes it possible to obtain a stimulation of the mucosal immune response.

The vaccine composition according to the invention can advantageously be provided in various pharmaceutical formulations which are particularly well suited to the route of administration and to the desired effect, i.e. obtaining a humoral, cellular and/or mucosal immune response.

A subject of the present invention is thus also a pharmaceutical formulation intended for oral administration, characterized in that it essentially consists of:

a core consisting of a vaccine composition as defined above embedded in a gelatin and a coating selected from the group consisting of a film-forming polymer which is soluble or expandable in water and soluble in solvents and which is selected from the group consisting of cellulose derivatives, polyvinylpyrrolidone, acrylic and methacrylic esters, polyethylene glycols, polyvinyl alcohols, vinylpyrrolidone/vinyl acetate copolymer, vinylpyrrolidone/polyvinyl alcohol copolymer and protein substances such as zein or gliadin.

Preferably, said film-forming agent is selected from the group consisting of cellulose ethers and esters, such as cellulose acetate, cellulose acetate phthalate, cellulose butyrate, ethylcellulose and methylcellulose.

According to one advantageous embodiment of said formulation, said film-forming polymer is combined with at least one plasticizer chosen from glycerol and esters thereof, high molecular weight polyethyleneglycols, ricin oil and citric, phthalic, adipic and sebacic acid esters.

Such a formulation, which is intended for oral administration, protects the recombinant Env protein (antigen) from degradation by gastric proteases and from the acid pH of the stomach. The coating dissolves in the alkaline pH of the intestine, which releases the antigen in the vicinity of Peyer's patches, which are the major sites of induction of mucosal immunity.

According to another advantageous embodiment of said formulation, said vaccine composition consists of a freeze-dried mixture of immunosomes, onto which a gp120/160 protein is anchored, with trehalose.

A preferred formulation intended to be administered orally comprises:

a core consisting of a freeze-dried mixture of immunosomes onto which a gp120/160 protein is anchored and of trehalose, embedded in gelatin and a coating consisting of a cellulose derivative, preferably cellulose acetate phthalate.

A subject of the present invention is thus also a pharmaceutical formulation intended for local administration to a mucous membrane (vaginal or rectal), characterized in that it essentially consists of a vaccine composition, as defined, above embedded in glycerol or a glycerol/glycerine-based mixture.

According to one advantageous embodiment of said formulation, said vaccine composition consists of a freeze-dried mixture of immunosomes, onto which a gp120/160 protein is anchored, with trehalose.

Besides the above arrangements, the invention comprises yet other arrangements which will emerge from the description which follows, which refers to examples of implementation of the method which is the subject of the present invention.

It should be clearly understood, however, that these examples are given only by way of illustration of the subject of the invention, of which they in no way constitute a limitation.

Example 1

Preparation of the EnvΔV3-GPGRAF Recombinant Protein

Partial Deletion of the V3 Loop

The env gene of HIV-1$_{LAI}$ is cloned into a baculoviral system; the variable sequences of the V3 loop were eliminated by introducing a modification into the env gene of pNL4-3, conserving only the nucleotides encoding the GPGRAF (SEQ ID NO: 1) hexapeptide and the two cysteines at the base of the loop.

This modification of the V3 loop was carried out with the aid of 4 oligonucleotides, They were hybridized so as to reconstitute the modified V3 loop and cloned directly between the Ase1 and Nhe1 restriction sites of an intermediate vector comprising the first 1035 nucleotides of the env gene, in such a way as to conserve only the GPGRAF (SEQ ID NO: 1) motif and the two cysteines of the V3 region.

The modification introduced into the gene was confirmed by sequencing the V3 region, and cloned into the previously constructed transfer vector pBacPAK env (7) in order to obtain the transfer vector pBacPAK envΔV3-GPGRAF. The latter made it possible to generate the envΔV3-GPGRAF recombinant baculovirus (7).

Expression of the Recombinant env Gene

Sf21 insect cells were infected with the *Autographa californica* nuclear polyhedrosis virus (AcNPV), as well as with the envΔV3-GPGRAF recombinant baculovirus. Three to four days post-infection, the cells were harvested, lysed in the presence of detergent and analysed by electrophoresis on 10% polyacrylamide gel, as well as by Western blot. The results showed that the cells infected with the envΔV3-GPGRAF recombinant baculovirus express a protein which has a molecular mass compatible with deletion. This protein is recognized by a human reference serum which is positive for the HIV-1 antigens (7).

Purification of ΔV3-GPGRAF Recombinant gp160

EnvΔV3-GPGRAF recombinant gp160 was purified by chromatography on a DEAE-cellulose column, followed by a purification on a *Lens culinaris* lectin column, from $2 \times 10^9$ Sf21 cells infected with the envΔV3-GPGRAF recombinant baculovirus. Analysis by electrophoresis showed that the protein was more than 80% pure.

Example 2

Preparation of a Pharmaceutical Formulation According to the Invention a. Preparation of Immunosomes with ΔV3-GPGRAF Recombinant gp160

The immunosomes were prepared by anchoring ΔV3-GPGRAF recombinant gp160 onto preformed liposomes in accordance with the method described in patent EP 47 480. The ΔV3-GPGRAF-immunosomes are particles of approximately 90 nm which are covered with ΔV3-GPGRAF-gp160.

b. Formulations of the Composition Obtained in a

For the oral immunizations, the ΔV3-GPGRAF-immunosomes are freeze-dried in the presence of threalose, and the antigen is introduced into a gelatin capsule. The capsule is coated with a mixture containing cellulose acetate phthalate, which protects the antigen from degradation by gastric proteases and from the acid pH of the stomach. The coating dissolves in the alkaline pH of the intestine, which releases the antigen in the vicinity of Peyer's patches, which are the major sites of induction of mucosal immunity.

For the immunizations via the vaginal or rectal route, the antigen is formulated in a glycerol/glycerine-based mixture which is solid at room temperature but which melts at physiological body temperature, thus gradually releasing the antigen.

Example 3

Demonstration of the Immunogenic and Vaccine Activity of a Formulation According to Example 2

Protocol for Immunization of C57/BL Mice

In this hyperimmunization protocol, 12 mice received four injections of immunosomes containing 25 μg of ΔV3-GPGRAF-gp160 intraperitoneally at 3-week intervals, followed by an intravenous booster. No adjuvant was used. Six control mice were subjected to the same protocol using PBS.

Evaluation by ELISA of the Immune Response Against the LAI, IIIB, MN and RF Strains Two weeks after the intravenous booster, the mice were bled by intracardiac puncture, and the sera were evaluated for the presence of IgM, IgG and IgA antibodies which react with the LAI, IIIB, MN and RF strains.

All the mice developed very high titres of IgG-type antibodies against each of the four strains tested, which were between 1/65 536 and 1/524 288. Tables I, II, III and IV show that the mice also developed antibodies of the three isotypes against four laboratory strains tested.

TABLE I

Humoral immune response of mice immunized with an immunosome-anchored ΔV3-GPGRAF-gp160 composition

| Mouse | Immuni-zations | Antigen | Titre by ELISA of antibodies directed against the LAI strain | | |
|---|---|---|---|---|---|
| | | | IgM | IgG | IgA |
| 1 | SIX | IMS-ΔV3-GPGRAF (25 μg) | 1/2 048 | 1/262 144 | 1/256 |
| 2 | " | IMS-ΔV3-GPGRAF (25 μg) | 1/1 024 | 1/262 144 | 1/256 |
| 3 | " | IMS-ΔV3-GPGRAF (25 μg) | 1/2 048 | 1/524 288 | 1/512 |
| 4 | " | IMS-ΔV3-GPGRAF (25 μg) | 1/512 | 1/131 072 | 1/256 |
| 5 | " | IMS-ΔV3-GPGRAF (25 μg) | 1/1 024 | 1/131 072 | 1/128 |
| 6 | " | IMS-ΔV3-GPGRAF (25 μg) | 1/2 048 | 1/262 144 | 1/256 |
| 7 | " | IMS-ΔV3-GPGRAF (25 μg) | 1/1 024 | 1/262 144 | 1/256 |
| 8 | " | IMS-ΔV3-GPGRAF (25 μg) | 1/1 024 | 1/65 538 | 1/128 |
| 9 | " | IMS-ΔV3-GPGRAF (25 μg) | 1/4 096 | 1/524 288 | 1/1 024 |
| 10 | " | IMS-ΔV3-GPGRAF (25 μg) | 1/4 096 | 1/524 288 | 1/1 024 |
| 11 | " | IMS-ΔV3-GPGRAF (25 μg) | 1/2 048 | 1/262 144 | 1/256 |
| 12 | " | IMS-ΔV3-GPGRAF (25 μg) | 1/2 048 | 1/262 144 | 1/256 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

TABLE II

Humoral immune response of mice immunized with an immunosome-anchored ΔV3-GPGRAF-gp160 composition

| Mouse | Immuni-zations | Antigen | Titre by ELISA of antibodies directed against the IIIB strain | | |
|---|---|---|---|---|---|
| | | | IgM | IgG | IgA |
| 1 | SIX | IMS-ΔV3-GPGRAF (25 μg) | 1/2 048 | 1/262 144 | 1/256 |
| 2 | " | IMS-ΔV3-GPGRAF (25 μg) | 1/1 024 | 1/262 144 | 1/256 |
| 3 | " | IMS-ΔV3-GPGRAF (25 μg) | 1/2 048 | 1/262 144 | 1/512 |
| 4 | " | IMS-ΔV3-GPGRAF (25 μg) | 1/1 024 | 1/131 072 | 1/256 |
| 5 | " | IMS-ΔV3-GPGRAF (25 μg) | 1/1 024 | 1/131 072 | 1/128 |
| 6 | " | IMS-ΔV3-GPGRAF (25 μg) | 1/2 048 | 1/131 072 | 1/256 |
| 7 | " | IMS-ΔV3-GPGRAF (25 μg) | 1/1 024 | 1/262 144 | 1/256 |
| 8 | " | IMS-ΔV3-GPGRAF (25 μg) | 1/1 024 | 1/65 536 | 1/128 |
| 9 | " | IMS-ΔV3-GPGRAF (25 μg) | 1/4 096 | 1/131 072 | 1/1 024 |
| 10 | " | IMS-ΔV3-GPGRAF (25 μg) | 1/4 096 | 1/131 072 | 1/1 024 |
| 11 | " | IMS-ΔV3-GPGRAF (25 μg) | 1/2 048 | 1/262 144 | 1/256 |
| 12 | " | IMS-ΔV3-GPGRAF (25 μg) | 1/2 048 | 1/131 072 | 1/256 |
| 13 | SIX | PBS | <1/32 | <1/32 | <1/32 |

TABLE II-continued

Humoral immune response of mice immunized with an immunosome-anchored ΔV3-GPGRAF-gp160 composition

| Mouse | Immunizations | Antigen | Titre by ELISA of antibodies directed against the IIIB strain | | |
|---|---|---|---|---|---|
| | | | IgM | IgG | IgA |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

TABLE III

Humoral immune response of mice immunized with an immunosome-anchored ΔV3-GPGRAF-gp160 composition

| Mouse | Immunizations | Antigen | Titre by ELISA of antibodies directed against the MN strain | | |
|---|---|---|---|---|---|
| | | | IgM | IgG | IgA |
| 1 | SIX | IMS-ΔV3-GPGRAF (25 μg) | 1/2 048 | 1/131 072 | 1/256 |
| 2 | " | IMS-ΔV3-GPGRAF (25 μg) | 1/1 024 | 1/131 072 | 1/256 |
| 3 | " | IMS-ΔV3-GPGRAF (25 μg) | 1/2 048 | 1/131 072 | 1/512 |
| 4 | " | IMS-ΔV3-GPGRAF (25 μg) | 1/1 024 | 1/65 536 | 1/256 |
| 5 | " | IMS-ΔV3-GPGRAF (25 μg) | 1/1 024 | 1/65 536 | 1/128 |
| 6 | " | IMS-ΔV3-GPGRAF (25 μg) | 1/2 048 | 1/65 536 | 1/256 |
| 7 | " | IMS-ΔV3-GPGRAF (25 μg) | 1/1 024 | 1/131 072 | 1/256 |
| 8 | " | IMS-ΔV3-GPGRAF (25 μg) | 1/1 024 | 1/65 536 | 1/128 |
| 9 | " | IMS-ΔV3-GPGRAF (25 μg) | 1/4 096 | 1/131 072 | 1/1 024 |
| 10 | " | IMS-ΔV3-GPGRAF (25 μg) | 1/4 096 | 1/131 072 | 1/1 024 |
| 11 | " | IMS-ΔV3-GPGRAF (25 μg) | 1/2 048 | 1/262 144 | 1/256 |
| 12 | " | IMS-ΔV3-GPGRAF (25 μg) | 1/2 048 | 1/131 072 | 1/256 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

TABLE IV

Humoral immune response of mice immunized with an immunosome-anchored ΔV3-GPGRAF-gp160 composition

| Mouse | Immunizations | Antigen | Titre by ELISA of antibodies directed against the RF strain | | |
|---|---|---|---|---|---|
| | | | IgM | IgG | IgA |
| 1 | SIX | IMS-ΔV3-GPGRAF (25 μg) | 1/1 024 | 1/131 072 | 1/128 |
| 2 | " | IMS-ΔV3-GPGRAF (25 μg) | 1/1 024 | 1/131 072 | 1/128 |
| 3 | " | IMS-ΔV3-GPGRAF (25 μg) | 1/2 048 | 1/131 072 | 1/256 |
| 4 | " | IMS-ΔV3-GPGRAF (25 μg) | 1/1 024 | 1/65 536 | 1/128 |
| 5 | " | IMS-ΔV3-GPGRAF (25 μg) | 1/1 024 | 1/65 536 | 1/64 |
| 6 | " | IMS-ΔV3-GPGRAF (25 μg) | 1/2 048 | 1/65 536 | 1/126 |
| 7 | " | IMS-ΔV3-GPGRAF (25 μg) | 1/1 024 | 1/131 072 | 1/126 |
| 8 | " | IMS-ΔV3-GPGRAF (25 μg) | 1/1 024 | 1/65 536 | 1/64 |
| 9 | " | IMS-ΔV3-GPGRAF (25 μg) | 1/1 024 | 1/131 072 | 1/256 |
| 10 | " | IMS-ΔV3-GPGRAF (25 μg) | 1/2 048 | 1/131 072 | 1/256 |
| 11 | " | IMS-ΔV3-GPGRAF (25 μg) | 1/2 048 | 1/262 144 | 1/128 |
| 12 | " | IMS-ΔV3-GPGRAF (25 μg) | 1/1 024 | 1/131 072 | 1/128 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

Determination of the Presence of Antibodies which are Capable of Neutralizing the Infectivity of Different Laboratory Strains The sera of mice immunized with the ΔV3-GPGRAF-gp160 immunosome were then evaluated for their potential for neutralizing the infectivity of the LAI, IIIB, MN, RF, LAV 43.01 and BAL strains. The neutralization assays are carried out using CEM cells. All the mice developed neutralizing antibodies ranging from 1/1024 to 1/126, as illustrated in Tables V and VI.

TABLE V

Titre of neutralizing antibodies directed against divergent strains of HIV-1 in mice immunized with the immunosome-anchored ΔV3-GPGRAF-gp160 vaccine composition

| Mouse | Immunizations | Antigen | Titre of antibodies which neutralize against 100 TCID$_{50}$ of: | | |
|---|---|---|---|---|---|
| | | | LAI | IIIB | RF |
| 1 | SIX | IMS-ΔV3-GPGRAF (25 μg) | 1/256 | 1/256 | 1/256 |
| 2 | " | IMS-ΔV3-GPGRAF (25 μg) | 1/256 | 1/256 | 1/256 |
| 3 | " | IMS-ΔV3-GPGRAF (25 μg) | 1/512 | 1/256 | 1/512 |
| 4 | " | IMS-ΔV3-GPGRAF (25 μg) | 1/256 | 1/128 | 1/256 |
| 5 | " | IMS-ΔV3-GPGRAF (25 μg) | 1/256 | 1/256 | 1/128 |
| 6 | " | IMS-ΔV3-GPGRAF (25 μg) | 1/256 | 1/126 | 1/256 |
| 7 | " | IMS-ΔV3-GPGRAF (25 μg) | 1/1 024 | 1/256 | 1/256 |
| 8 | " | IMS-ΔV3-GPGRAF (25 μg) | 1/64 | 1/32 | 1/128 |
| 9 | " | IMS-ΔV3-GPGRAF (25 μg) | 1/256 | 1/256 | 1/1 024 |

TABLE V-continued

Titre of neutralizing antibodies directed against divergent strains of HIV-1 in mice immunized with the immunosome-anchored ΔV3-GPGRAF-gp160 vaccine composition

| Mouse | Immuni-zations | Antigen | Titre of antibodies which neutralize against 100 $TCID_{50}$ of: | | |
|---|---|---|---|---|---|
| | | | LAI | IIIB | RF |
| 10 | " | IMS-ΔV3-GPGRAF (25 μg) | 1/256 | 1/126 | 1/1 024 |
| 11 | " | IMS-ΔV3-GPGRAF (25 μg) | 1/512 | 1/512 | 1/256 |
| 12 | " | IMS-ΔV3-GPGRAF (25 μg) | 1/256 | 1/126 | 1/256 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

TABLE VI

Titre of neutralizing antibodies directed against divergent strains of HIV-1 in mice immunized with the immunosome-anchored ΔV3-GPGRAF-gp160 vaccine composition

| Mouse | Immuni-zations | Antigen | Titre of antibodies which neutralize against 100 $TCID_{50}$ of: | | |
|---|---|---|---|---|---|
| | | | LAV 43.01 | MN | BAL |
| 1 | SIX | IMS-ΔV3-GPGRAF (25 μg) | 1/256 | 1/126 | 1/126 |
| 2 | " | IMS-ΔV3-GPGRAF (25 μg) | 1/256 | 1/126 | 1/64 |
| 3 | " | IMS-ΔV3-GPGRAF (25 μg) | 1/1 024 | 1/256 | 1/256 |
| 4 | " | IMS-ΔV3-GPGRAF (25 μg) | 1/256 | 1/128 | 1/126 |
| 5 | " | IMS-ΔV3-GPGRAF (25 μg) | 1/256 | 1/256 | 1/128 |
| 6 | " | IMS-ΔV3-GPGRAF (25 μg) | 1/256 | 1/126 | 1/256 |
| 7 | " | IMS-ΔV3-GPGRAF (25 μg) | 1/1 024 | 1/256 | 1/256 |
| 8 | " | IMS-ΔV3-GPGRAF (25 μg) | 1/32 | 1/32 | 1/64 |
| 9 | " | IMS-ΔV3-GPGRAF (25 μg) | 1/256 | 1/256 | 1/256 |
| 10 | " | IMS-ΔV3-GPGRAF (25 μg) | 1/256 | 1/126 | 1/126 |
| 11 | " | IMS-ΔV3-GPGRAF (25 μg) | 1/1 024 | 1/512 | 1/256 |
| 12 | " | IMS-ΔV3-GPGRAF (25 μg) | 1/256 | 1/126 | 1/126 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

Evaluation of the Neutralizing Power of the Sera Against Six Primary Isolates

Finally, the neutralizing power of the mouse sera was determined against six primary isolates: 03908, 65869, 65965, 65870, 65871 and 3929, generated from coculture of lymphocytes from patients at various stages of the disease, with lymphocytes from seronegative donors. The neutralization assays were carried out using non-stimulated PBLs. All the mice developed antibodies which were capable of neutralizing the infectivity of primary isolates. By way of example, see Tables VII and VIII. The titres were generally very high, these titres being between 1/512 and 1/256 against five of the six primary isolates tested. Isolate 65869 proved to be more resistant to neutralization. The titres were 1/64 and 1/32 and <1/32 in four of the sera. This isolate came from a patient in the terminal phase of the disease, and the virus induced gigantic syncytia in the cell cultures.

TABLE VII

Titre of neutralizing antibodies directed against divergent strains of HIV-1 in mice immunized with the immunosome-anchored ΔV3-GPGRAF-gp160 vaccine composition

| Mouse | Immuni-zations | Antigen | Titre of antibodies which neutralize against 100 $TCID_{50}$ of: | | |
|---|---|---|---|---|---|
| | | | # 03908 | # 65869 | # 65965 |
| 1 | SIX | IMS-ΔV3-GPGRAF (25 μg) | 1/126 | <1/32 | 1/64 |
| 2 | " | IMS-ΔV3-GPGRAF (25 μg) | 1/64 | 1/32 | 1/126 |
| 3 | " | IMS-ΔV3-GPGRAF (25 μg) | 1/256 | 1/32 | 1/126 |
| 4 | " | IMS-ΔV3-GPGRAF (25 μg) | 1/126 | <1/32 | 1/256 |
| 5 | " | IMS-ΔV3-GPGRAF (25 μg) | 1/256 | 1/64 | 1/126 |
| 6 | " | IMS-ΔV3-GPGRAF (25 μg) | 1/512 | 1/32 | 1/512 |
| 7 | " | IMS-ΔV3-GPGRAF (25 μg) | 1/256 | 1/64 | 1/256 |
| 8 | " | IMS-ΔV3-GPGRAF (25 μg) | <1/32 | <1/32 | <1/32 |
| 9 | " | IMS-ΔV3-GPGRAF (25 μg) | 1/512 | <1/32 | 1/256 |
| 10 | " | IMS-ΔV3-GPGRAF (25 μg) | 1/256 | 1/32 | 1/126 |
| 11 | " | IMS-ΔV3-GPGRAF (25 μg) | 1/512 | 1/32 | 1/256 |
| 12 | " | IMS-ΔV3-GPGRAF (25 μg) | 1/256 | 1/32 | 1/126 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

TABLE VIII

Titre of neutralizing antibodies directed against divergent strains of HIV-1 in mice immunized with the immunosome-anchored ΔV3-GPGRAF-gp160 vaccine composition

| Mouse | Immuni-zations | Antigen | Titre of antibodies which neutralize against 100 $TCID_{50}$ of: | | |
|---|---|---|---|---|---|
| | | | # 65870 | # 65871 | # 3929 |
| 1 | SIX | IMS-ΔV3-GPGRAF (25 μg) | 1/64 | 1/126 | 1/64 |
| 2 | " | IMS-ΔV3-GPGRAF (25 μg) | 1/126 | 1/126 | 1/126 |
| 3 | " | IMS-ΔV3-GPGRAF (25 μg) | 1/126 | 1/256 | 1/256 |
| 4 | " | IMS-ΔV3-GPGRAF (25 μg) | 1/256 | 1/128 | 1/126 |
| 5 | " | IMS-ΔV3-GPGRAF (25 μg) | 1/256 | 1/126 | 1/126 |

TABLE VIII-continued

Titre of neutralizing antibodies directed against divergent strains of HIV-1 in mice immunized with the immunosome-anchored ΔV3-GPGRAF-gp160 vaccine composition

| Mouse | Immunizations | Antigen | Titre of antibodies which neutralize against 100 $TCID_{50}$ of: | | |
|---|---|---|---|---|---|
| | | | # 65870 | # 65871 | # 3929 |
| 6 | " | IMS-ΔV3-GPGRAF (25 µg) | 1/256 | 1/64 | 1/256 |
| 7 | " | IMS-ΔV3-GPGRAF (25 µg) | 1/126 | 1/256 | 1/256 |
| 8 | " | IMS-ΔV3-GPGRAF (25 µg) | <1/32 | <1/32 | <1/32 |
| 9 | " | IMS-ΔV3-GPGRAF (25 µg) | 1/256 | 1/256 | 1/256 |
| 10 | " | IMS-ΔV3-GPGRAF (25 µg) | 1/256 | 1/126 | 1/126 |
| 11 | " | IMS-ΔV3-GPGRAF (25 µg) | 1/512 | 1/512 | 1/256 |
| 12 | " | IMS-ΔV3-GPGRAF (25 µg) | 1/256 | 1/126 | 1/126 |
| 13 | SIX | PBS | <1/32 | <1/32 | <1/32 |
| 14 | " | " | <1/32 | <1/32 | <1/32 |
| 15 | " | " | <1/32 | <1/32 | <1/32 |
| 16 | " | " | <1/32 | <1/32 | <1/32 |
| 17 | " | " | <1/32 | <1/32 | <1/32 |
| 18 | " | " | <1/32 | <1/32 | <1/32 |

These results show that partially deleting the V3 loop while keeping the conserved sequence GPGRAF (SEQ ID NO: 1) promotes the induction of wide-ranging antibodies which are capable of neutralizing various laboratory strains, but also various primary isolates.

Similar results are obtained with the protein which contains a total deletion of the V3 loop.

REFERENCES (1) Emini E., Schleif W., Numberg, J. et al. 1992. Prevention of HIV-1 infection in chimpanzees by gp120 V3 domain-specific monoclonal antibody. Nature 355: 728–30.

(2) Girard M. P., Kieny M., Pinter A., et al. 1991. Immunization of chimpanzees confers protection against challenge with human immunodeficiency virus. Proc. Nat. Acad. Sci. USA 88:542–46.

(3) Nara P. L., Garrity R. R., Goudsmit J. et al. 1991. Neutralization of HIV-1: a paradox of humoral proportion. FASEB J. 5:2437–55.

(4) Palker T. J., Claar M. E., Langlois A. J et al. 1988. Type-specific neutralization of the human immunodeficiency virus with antibodies to env-coded peptides. Proc. Nat. Acad. Sci. USA 85:1932–6.

(5) Javaherian K., Langlois J., McDonald C. et al. 1989. Principal neutralization domain of the human immunodeficiency virus type 1 envelope protein. Proc. Nat. Acad. Sci. USA 86:6768–72.

(6) Lucinda A., Dubay J. W., Morris J. F. et al. 1992. V3 loop region of the HIV-1 gp120 envelope protein is essential for virus infectivity. Virology 187:423–32.

(7) Lavallée Claude and Lise Thibiodeau (1996) Clonage, expression et caractérisation de gp160 du VIH-1, portant des délétions partielles ou totales dans la boucle V3. [Cloning, expression and characterization of HIV-1 gp160, bearing partial or total deletions in the V3 loop] 1996 C.R. Acad. Sci. Paris 319:983–990.

As emerges from the above, the invention is in no way limited to those of its modes of implementation, execution and application which have just been described more explicitly; on the contrary, it embraces all the variants thereof which may occur to persons skilled in the art, without departing from the context or the scope of the present invention.

The invention claimed is:

1. An immunogenic composition formulated for local administration directly to a mucous membrane comprising a recombinant HIV-1 envelope protein comprising a mutated V3 loop, wherein the mutated V3 loop comprises the GPGRAF (SEQ ID NO: 1) hexamer sequence flanked by the two basal cysteines but lacks all or a portion of the rest of the V3 loop, said recombinant HIV-1 envelope protein being anchored onto preformed liposomes.

2. The immunogenic composition of claim 1 further comprising adjuvants.

3. The immunogenic composition of claim 2, wherein the adjuvants are derivatives comprising divalent or trivalent ions or muramylpeptide derivatives.

4. The immunogenic composition of claim 3, wherein the derivatives comprising divalent or trivalent ions are aluminum hydroxide or calcium phosphate.

5. The immunogenic composition of claim 1, wherein the envelope protein is anchored onto unilamellar synthetic lipid vesicles.

6. The immunogenic composition of claim 1 wherein the vesicles comprise a molar ratio of phosphatidylcholine to cholesterol of about 8:1, and which have a size of between 70 and 150 nm.

7. The immunogenic composition of claim 6, wherein the size of the vesicles is about 90 nm.

8. The immunogenic composition of claim 1, wherein the envelope protein is selected from the group consisting of gp160 and gp120 Env proteins.

9. The immunogenic composition of claim 1, wherein the immunogenic composition is formulated for administering rectally or vaginally.

10. The immunogenic composition of claim 1, wherein the immunogenic composition comprises at least glycerol or a glycerol/glycerine-based mixture.

11. The immunogenic composition of claim 1 further comprising trehalose.

* * * * *